(12) United States Patent
Pianca et al.

(10) Patent No.: US 8,332,049 B2
(45) Date of Patent: Dec. 11, 2012

(54) IMPLANTABLE MULTI-LEAD ELECTRIC STIMULATION SYSTEM AND METHODS OF MAKING AND USING

(75) Inventors: Anne Margaret Pianca, Santa Monica, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 802 days.

(21) Appl. No.: 12/413,429

(22) Filed: Mar. 27, 2009

(65) Prior Publication Data

US 2009/0248111 A1 Oct. 1, 2009

Related U.S. Application Data

(60) Provisional application No. 61/041,066, filed on Mar. 31, 2008.

(51) Int. Cl.
*A61N 1/00* (2006.01)
(52) U.S. Cl. ......... 607/122; 607/116; 607/119; 607/123
(58) Field of Classification Search .................... 607/122
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,855,144 B2 * | 2/2005 | Lesh | 606/41 |
| 6,871,101 B2 * | 3/2005 | Zhang et al. | 607/122 |
| 7,244,150 B1 | 7/2007 | Brase et al. | |
| 2003/0114905 A1 | 6/2003 | Kuzma | |
| 2003/0163184 A1* | 8/2003 | Scheiner et al. | 607/122 |
| 2004/0059392 A1 | 3/2004 | Parramon et al. | |
| 2005/0065570 A1* | 3/2005 | Stein et al. | 607/37 |
| 2005/0165465 A1 | 7/2005 | Pianca et al. | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0219595 A1 | 9/2007 | He | |
| 2007/0239243 A1 | 10/2007 | Moffitt et al. | |
| 2008/0051672 A1* | 2/2008 | McCabe et al. | 600/515 |
| 2008/0071320 A1 | 3/2008 | Brase | |

OTHER PUBLICATIONS

U.S. Appl. No. 11/238,240, filed Sep. 29, 2005.

* cited by examiner

*Primary Examiner* — Niketa Patel
*Assistant Examiner* — Minh Duc Pham
(74) *Attorney, Agent, or Firm* — Frommer Lawrence & Haug LLP; Patrick R. Turner (57) ABSTRACT

A multi-lead system includes a first lead and a second lead. The first lead includes a distal end and a first plurality of electrodes disposed along the distal end of the first lead. The first plurality of electrodes are configured and arranged in a first electrode axis. The second lead includes a distal end and a proximal end. A second plurality of electrodes is disposed along the distal end of the second lead. The second plurality of electrodes are configured and arranged in a second electrode axis. The second lead also includes at least one bend between the distal end and the proximal end to allow for linear alignment of the first electrode axis with the second electrode axis to form a combination electrode axis when the first lead and the second lead are implanted.

20 Claims, 11 Drawing Sheets

Fig. 11

IMPLANTABLE MULTI-LEAD ELECTRIC STIMULATION SYSTEM AND METHODS OF MAKING AND USING

CROSS-REFERENCE TO RELATED APPLICATIONS

This application is a utility patent application based on a previously filed U.S. Provisional Patent Application Ser. No. 61/041,066 filed on Mar. 31, 2008, the benefit of which is hereby claimed under 35 U.S.C. §119(e) and incorporated herein by reference.

TECHNICAL FIELD

The present invention is directed to the area of implantable electrical stimulation systems and methods of making and using the systems. The present invention is also directed to implantable electrical stimulation systems that include a plurality of leads, each lead having a plurality of electrodes at a distal end, the plurality of leads configured and arranged to linearly align the electrodes of multiple leads to collectively form a combination electrode array, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a multi-lead system includes a first lead and a second lead. The first lead includes a distal end and a first plurality of electrodes disposed along the distal end of the first lead. The first plurality of electrodes are configured and arranged in a first electrode axis. The second lead includes a distal end and a proximal end. A second plurality of electrodes is disposed along the distal end of the second lead. The second plurality of electrodes are configured and arranged in a second electrode axis. The second lead also includes at least one bend between the distal end and the proximal end to allow for linear alignment of the first electrode axis with the second electrode axis to form a combination electrode axis when the first lead and the second lead are implanted.

In another embodiment, an electrical stimulating system includes a plurality of leads, at least one control module configured and arranged to electrically couple to each of the leads, and a connector for receiving at least one of the leads. Each of the plurality of leads has a distal end and a proximal end and includes a plurality of electrodes disposed on the distal end of the lead and a plurality of terminals disposed on the proximal end of the lead. At least one lumen extends from the proximal end to the distal end of each lead. A plurality of conductor wires extend along each of the plurality of leads to couple the plurality of electrodes electrically to the plurality of terminal. At least one of the plurality of leads includes at least one bend disposed between the plurality of electrodes and the plurality of terminals. The at least one bend is configured and arranged to linearly align electrodes on at least two of the plurality of leads to form a combination electrode array when the plurality of leads are implanted. The at least one control module includes a housing and an electronic subassembly disposed in the housing. The connector includes a connector housing defining at least one port for receiving the proximal end of at least one of the leads and a plurality of connector contacts disposed in the connector housing. The connector contacts are configured and arranged to couple to at least one terminal on the proximal end of the lead.

In yet another embodiment, a method for stimulating patient tissue includes implanting a first lead into a patient, implanting a second lead into a patient, coupling the first and second leads to at least one control module, and providing electrical signals from at least one of the control modules to electrically stimulate patient tissue. The first lead includes a first plurality of electrodes disposed in a first electrode axis on a distal end of the first lead. The first plurality of electrodes is electrically coupled to a first plurality of terminals disposed on a proximal end of the first lead. The first lead also includes at least one bend between the first plurality of electrodes and the first plurality of terminals. The second lead includes a second plurality of electrodes disposed in a second electrode axis on a distal end of the second lead. The second plurality of electrodes is electrically coupled to a second plurality of terminals disposed on a proximal end of the second lead. The at least one bend of the first lead is configured and arranged to allow for linear alignment of the first electrode axis with the second electrode axis to form a combination electrode axis when the first and second leads are implanted into the patient. The at least one control module electrically stimulates patient tissue using at least one of the electrodes on at least one of the leads.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a plurality of leads, each lead having a plurality of electrodes at a distal end, the plurality of leads configured and arranged to linearly align the electrodes of multiple leads to collectively form a combination electrode array, as well as methods of making and using the leads and electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
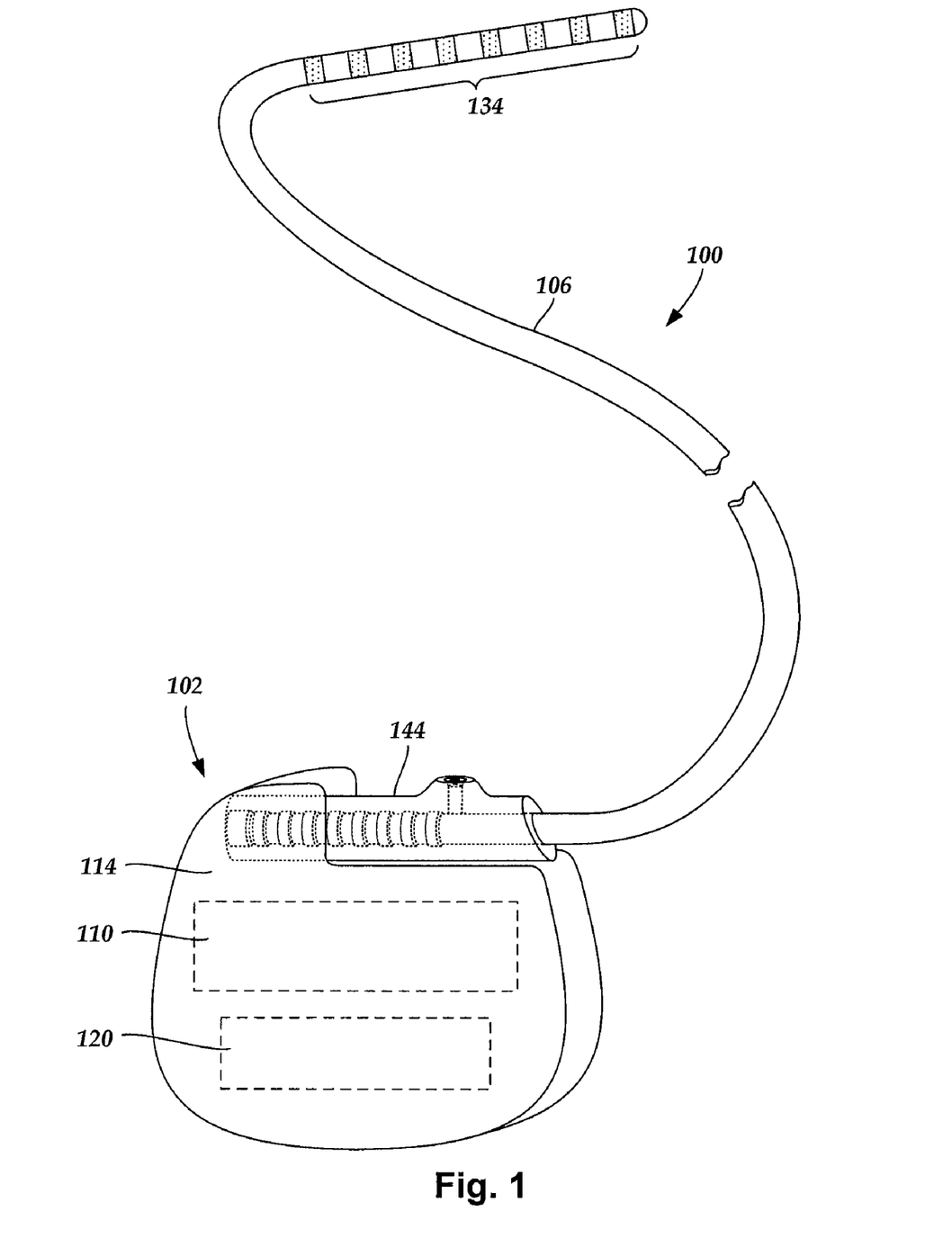
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead body 106 ("lead") coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts on the control module 102 and terminals (e.g., 210 in FIG. 2A and 236 of FIG. 2B) on each of the one or more leads 106. In at least some embodiments, a lead is isodiametric along a longitudinal length of the lead body 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106.

Terminals (e.g., 210 in FIG. 2A and 236 of FIG. 2B) are typically disposed at the proximal end of the one or more leads 106 of the electrical stimulation system 100 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In at least some embodiments, each terminal (e.g., 210 in FIG. 2A and 236 of FIG. 2B) is only connected to one electrode 134. The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet rod to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
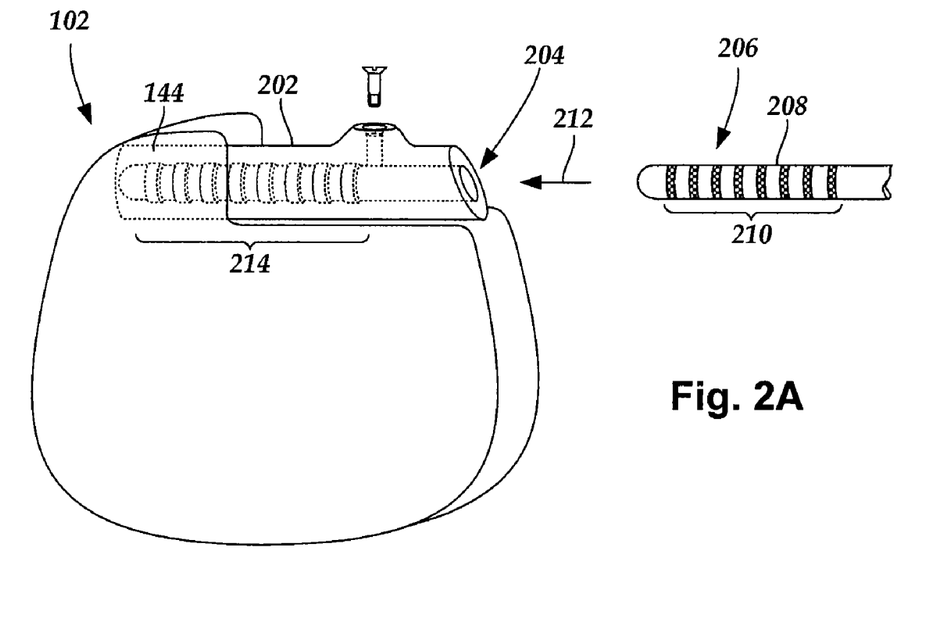
FIG. 2A is a schematic view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat. No. 7,244,150 and U.S. patent application Ser. No. 11/532,844, which are incorporated by reference.

Figure 2B:
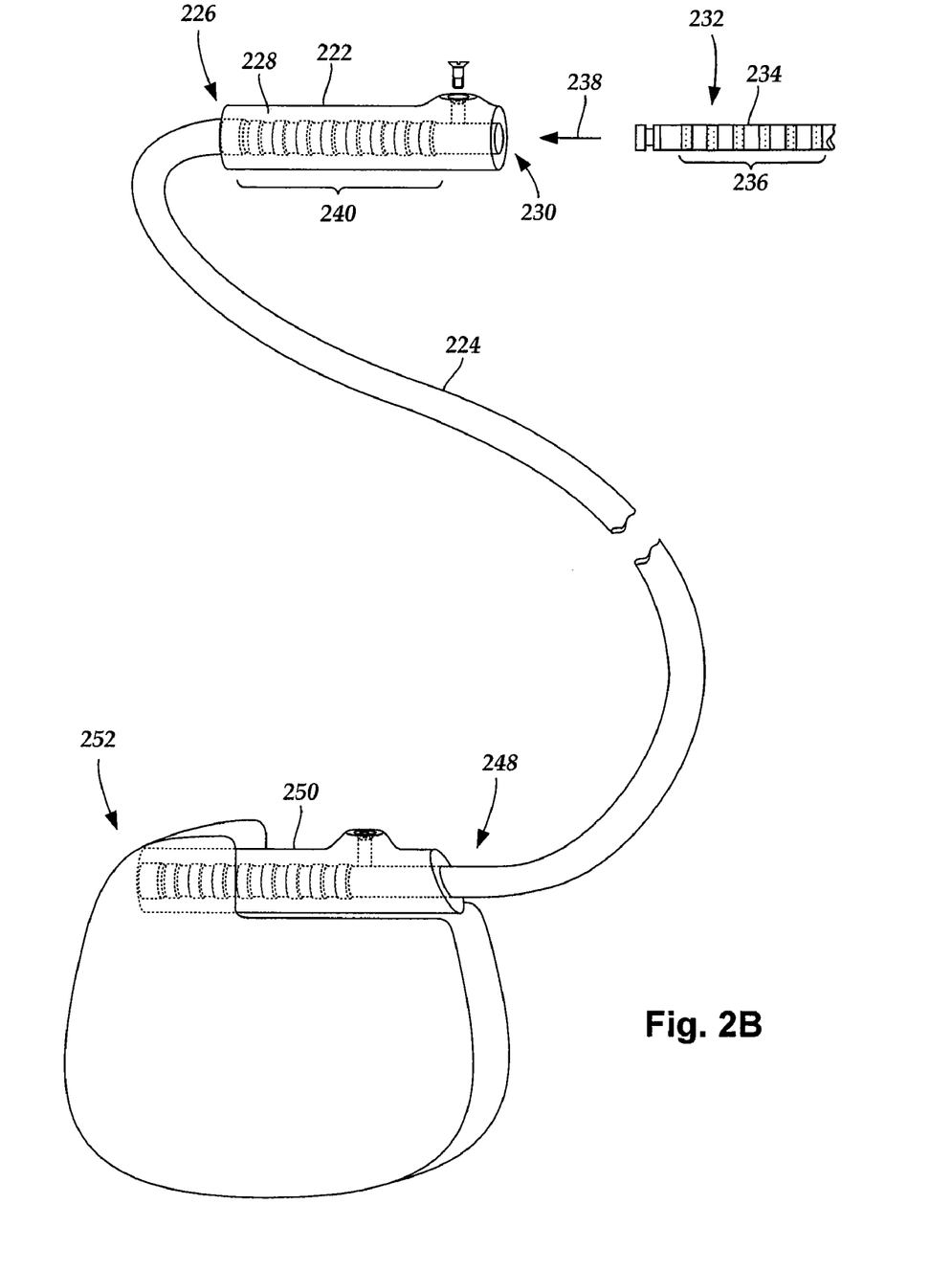
FIG. 2B is a schematic view of one embodiment of a proximal portion of a lead and a lead extension for an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

Sometimes a patient may be experiencing pain that extends to an area greater in length than the length of a conventional array of electrodes (e.g., 134 of FIG. 1) disposed on a distal end of a conventional lead. For example, a patient may experience pain originating from an area that spans multiple vertebral bodies. One way to increase stimulation coverage is to provide a lead with a greater length and increase the number of electrodes disposed on the lead. Another way to increase stimulation coverage is to provide a lead with a greater length and either increase the amount of space between adjacent electrodes, or to increase the size of one or more of the electrodes. However, when the amount of space between adjacent electrodes is increased or the size of one or more of the electrodes in increased, linear electrode density may decrease to a sub-therapeutic level. Additionally, the precision of current steering may also be reduced.

Figure 3A:
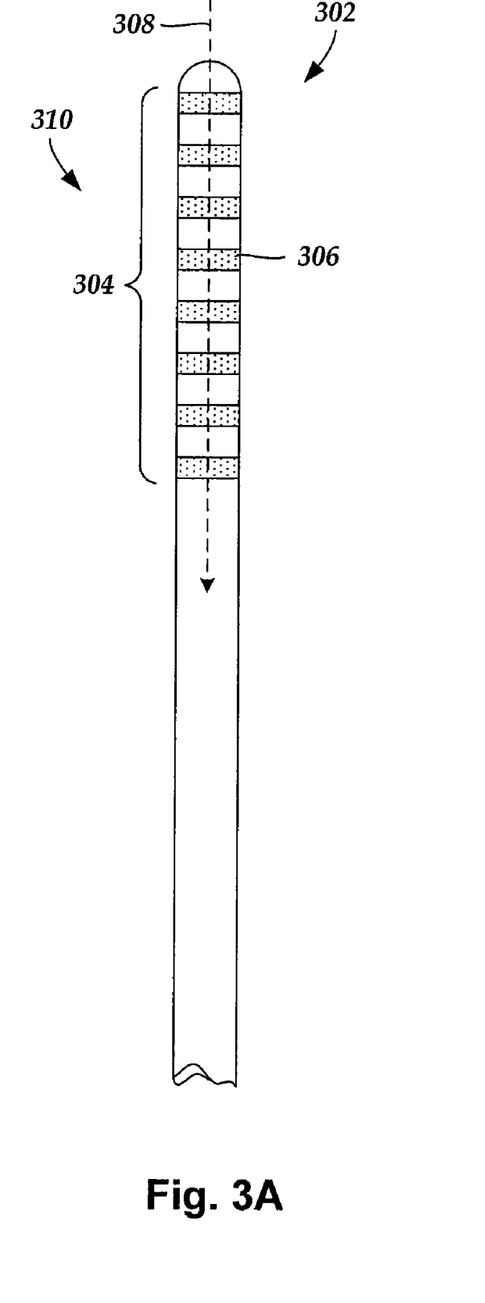
FIG. 3A is a schematic side view of one embodiment of a distal end of a lead of an electrical stimulation system, according to the invention.
Figure 3B:
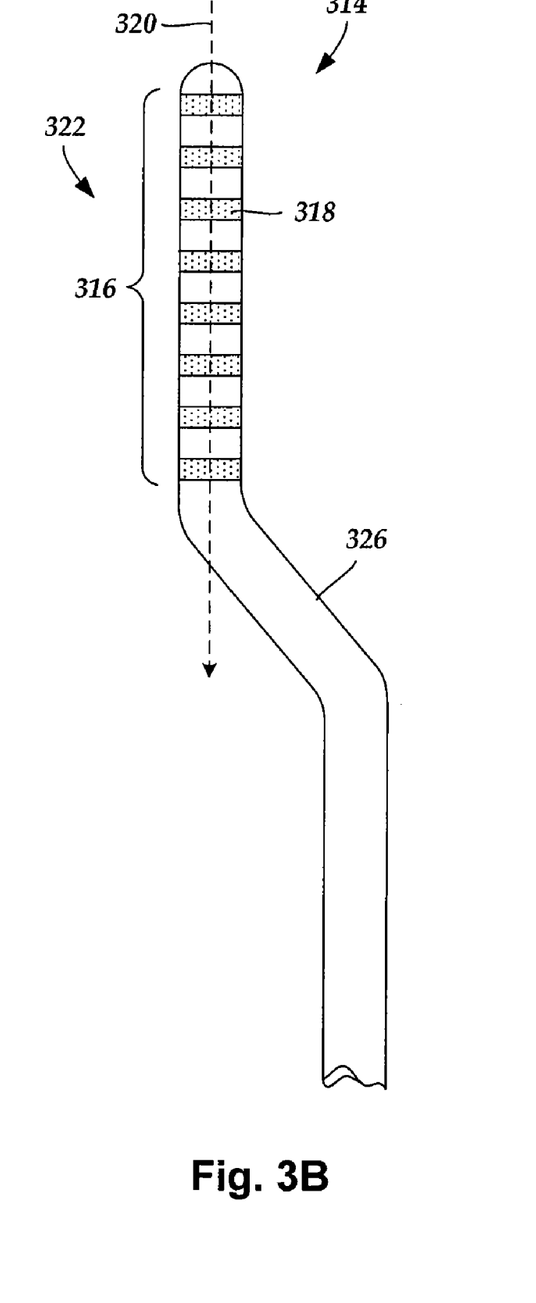
FIG. 3B is a schematic side view of one embodiment of a distal end of a lead with a bend proximal to an array of electrodes, according to the invention.

In at least some embodiments, a plurality of leads, each lead including a plurality of electrodes disposed along an electrode axis, are configured and arranged so that the leads can be positioned in proximity to one another with the electrode axes preferably linearly aligned to form a combination electrode array along a combination electrode axis with a linear length that is greater than the linear length of any one of the individual electrode axes. FIG. 3A is a schematic side view of one embodiment of a lead 302. The lead 302 includes a plurality of electrodes 304, such as electrode 306, disposed along an electrode axis 308 on a distal end 310 of the lead 302. In FIG. 3A and in subsequent figures, the center portions of leads are shown as being straight and extending parallel to corresponding electrode axes. In alternate embodiments, center portions are flexible and may or may not extend in one or more directions parallel to a corresponding electrode array. FIG. 3B is a schematic side view of one embodiment of a lead 314 that includes a plurality of electrodes 316, such as electrode 318, disposed along an electrode axis 320 on a distal end 322 of the lead 314. The lead 314 also includes a bend 326, preferably near the distal end 322, but the bend 326 may be positioned anywhere between the distal and proximal ends of the lead 314. In at least some embodiments, the bend 326 is straightenable, as discussed below with reference to FIG. 4B. Note that, in FIG. 3B and in subsequent figures, the shape of the bend 326 is exaggerated for clarity of illustration.

Figure 3C:
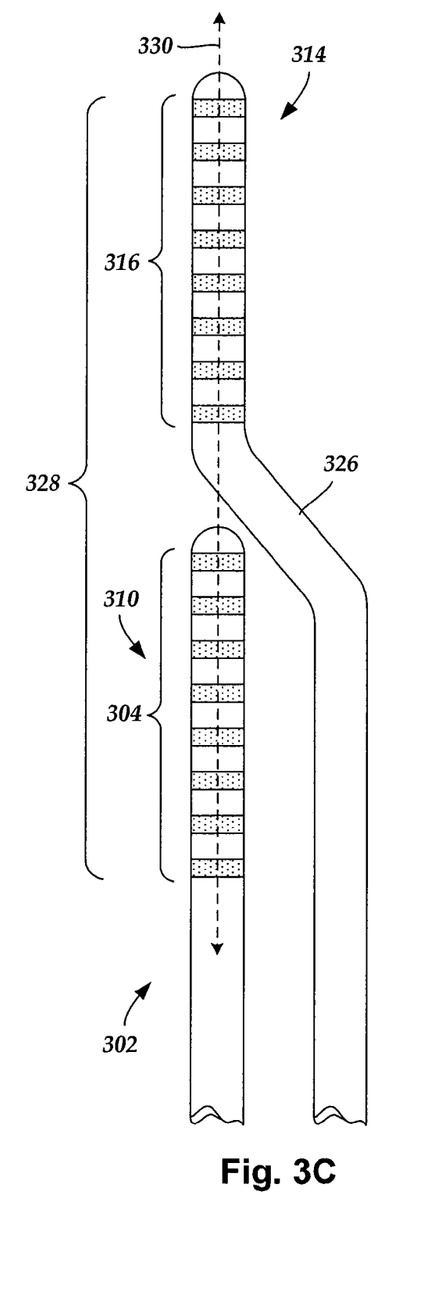
FIG. 3C is a schematic side view of one embodiment of electrodes disposed on the distal ends of the leads shown in FIGS. 3A and 3B and aligned along a combination electrode axis to form a combination electrode array, according to the invention.

FIG. 3C is a schematic side view of one embodiment of a combination electrode array 328 formed from electrodes disposed on the lead 302 and the lead 314. The bend 326 of the lead 314 is positioned near the distal end 310 of the lead 302 with the plurality of electrodes 304 of the lead 302 preferably linearly aligned with the plurality of electrodes 316 of the lead 314 along a combination electrode axis 330 to form the combination electrode array 328. Note that, in FIG. 3C and in subsequent figures, the center-to-center distance between the portions of two or more leads proximal to the electrodes is exaggerated for clarity of illustration. In some embodiments, the portions of the two or more leads proximal to the electrodes may be less than the diameter on the leads. In other embodiments, the portions of the two or more leads proximal to the electrodes may be equal to, or greater than, the diameter on the leads. In at least some embodiments, the portions of the two or more leads proximal to the electrodes are in contact with one another.

Figure 3D:
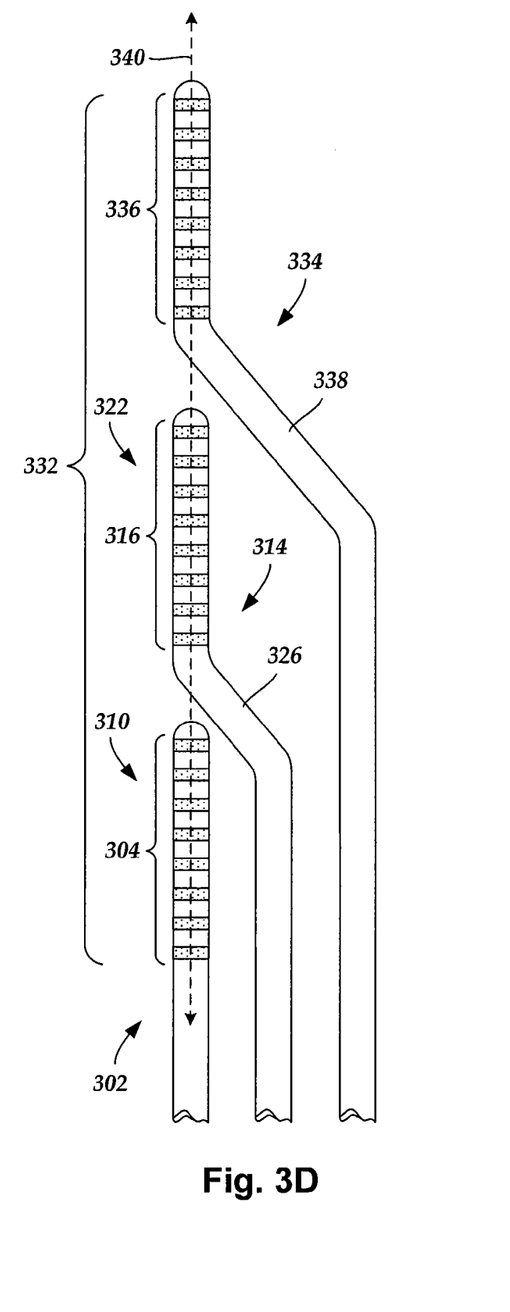
FIG. 3D is a schematic side view of one embodiment of electrodes disposed on the distal ends of the leads shown in FIGS. 3A and 3B aligned along a combination electrode axis with electrodes disposed on a distal end of a third lead to form a combination electrode array, according to the invention.

FIG. 3D shows one embodiment of a combination electrode array 332 formed from electrodes disposed on three leads 302, 314, and 334. The leads 302, 314, and 334 are positioned in proximity to one another. The lead 302 includes the plurality of electrodes 304, the lead 314 includes the plurality of electrodes 316, and the lead 334 includes a plurality of electrodes 336. The lead 334 further includes a bend 338 configured and arranged to bend proximate to the distal end 322 of the lead 314 which, in turn, has a bend 326 configured and arranged to bend proximate to the distal end 310 of the lead 302 with the three pluralities of electrodes 304, 316, and 336 preferably linearly aligned along a combination electrode axis 340 to form the combination electrode array 332.

Any number of leads can be used in a like manner to form a combination electrode array 328 or 332. For example, there can be two, three, four, five, six, seven, eight, nine, ten, twelve, fourteen, sixteen, or more leads. As will be recognized, other numbers of leads may also be used. In FIGS. 3C-3D and in subsequent figures, two or more leads with electrodes forming a combination electrode array are shown oriented with portions of the leads toward the proximal ends of the leads that are positioned parallel to one another. In at least some embodiments, the portions of the two or more leads toward the proximal ends of the leads are not parallel to one another.

Figure 4A:
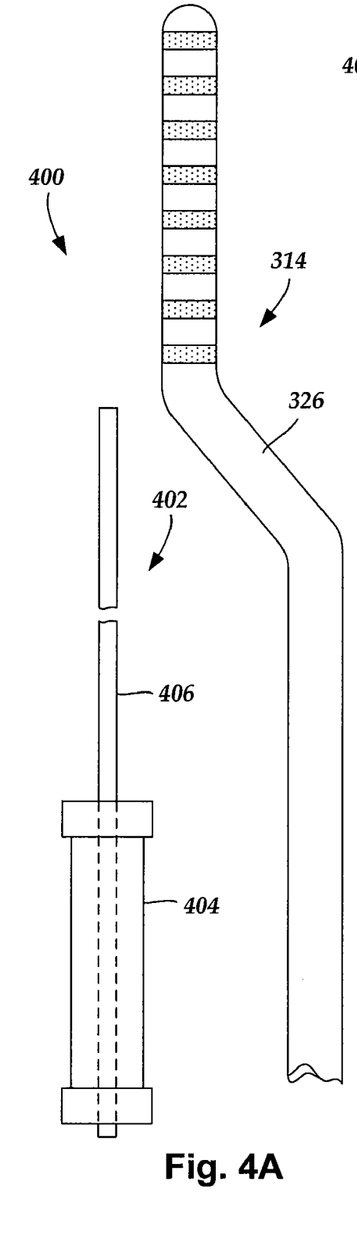
FIG. 4A is a schematic side view of one embodiment of a distal end of a lead and a stylet of an electrical-stimulation implantation system, according to the invention.

In at least some embodiments, multiple leads with electrodes that collectively form a combination electrode array can be individually implanted into a patient. FIG. 4A shows a schematic side view of one embodiment of an electrical-stimulation implantation system 400 that includes a stylet 402 and the lead 314. The stylet 402 includes a stylet handle 404 and an insertion rod 406. In at least some embodiments, the stylet 402 can be used to facilitate implantation of the lead 314 into a patient. In at least some embodiments, the insertion rod 406 can be inserted into one or more lumens and extended along at least a portion of a longitudinal length of the lead 314 to provide increased rigidity and the stylet handle 404 can be used to guide the insertion rod 406. In FIG. 4A and in subsequent figures, the insertion rod 406 is shown as an elongated rectangle. In at least some embodiments, the cross-sectional shape of the stylet 402, the insertion rod 406, the stylet handle 404, the lead 314, and/or the one or more lumens (not shown) of the lead 414 may be of many different shapes, including, circular, semi-circular, oblong, square, rectangular, triangular, star-shaped, or other suitable shape. In at least some embodiments, the cross-sectional shape of the lumen (not shown) into which the insertion rod 406 is inserted matches the cross-sectional shape of the insertion rod 406.

Figure 4B:
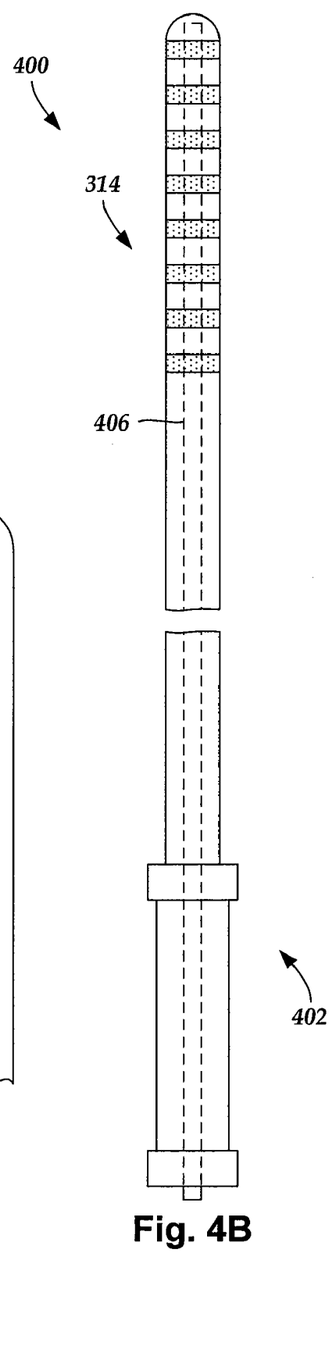
FIG. 4B is a schematic side view of the embodiment of the electrical-stimulation implantation system shown in FIG. 4A with an insertion rod inserted in a proximal end of a lead, according to the invention.
Figure 4C:
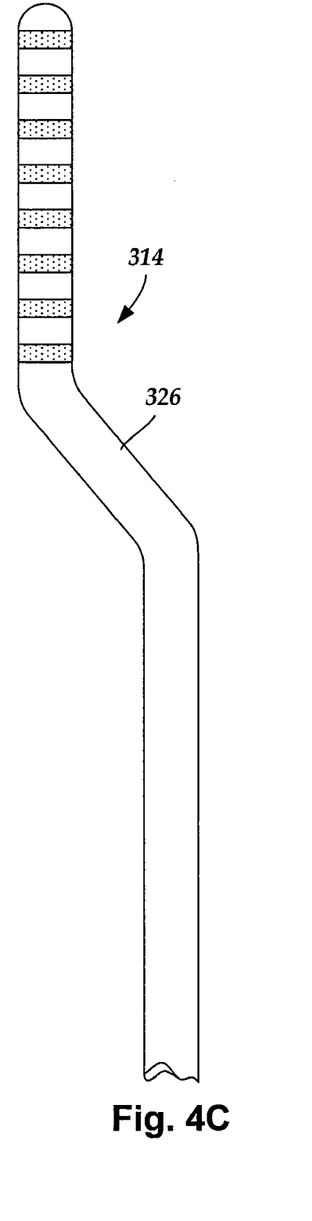
FIG. 4C is a schematic side view of the lead shown in FIG. 4B with a bend reformed in the lead after removal of the insertion rod shown in FIG. 4B, according to the invention.

In some embodiments, when an insertion rod is inserted into a lumen of a lead, the rigidity of the insertion rod can cause one or more bends in the lead to straighten when the insertion rod extends within the one or more bends. FIG. 4B shows one embodiment of the electrical-stimulation implantation system 400 with the insertion rod 406 of the stylet 402 inserted into a lumen (not shown) in a proximal end of the lead 314. As shown in FIG. 4B, when the insertion rod 406 extends through the bend (326 in FIG. 4A), the bend straightens. FIG. 4C shows a schematic side view of the lead 314 following removal of the insertion rod (406 in FIG. 4B). As shown in FIG. 4C, when the insertion rod (406 in FIG. 4B) is removed from the lead 314, the bend 326 reforms. In at least some embodiments, once the lead 314 is implanted and the bend 326 reforms, another lead, either with or without a bend, can be implanted in proximity to the lead 314 so that the electrodes of the subsequently implanted lead align linearly with the lead 314, as shown in FIG. 3C.

Figure 5:
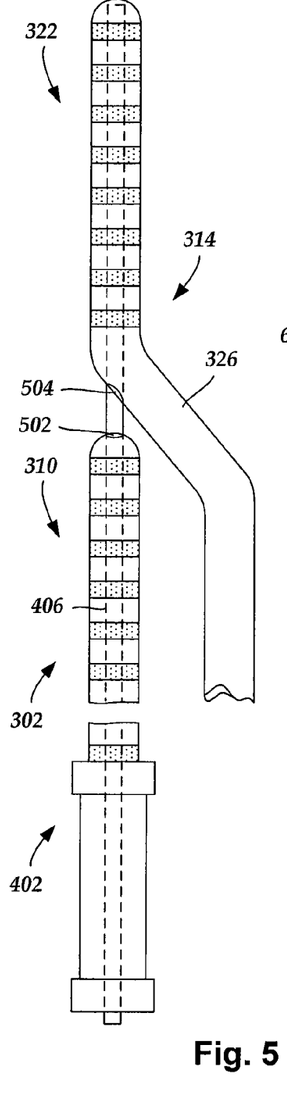
FIG. 5 is a schematic side view of another embodiment of the electrical-stimulation implantation system shown in FIG. 4A with an insertion rod inserted in a proximal end of a first lead and extending through an outlet port defined in a distal end of the first lead and into an inlet port defined in a bend of a second lead, according to the invention.

In other embodiments, multiple leads with electrodes that collectively form a combination electrode array can be jointly implanted into a patient. FIG. 5 shows a schematic side view of another embodiment of the electrical-stimulation implantation system 400 with the insertion rod 406 inserted in a proximal end of the lead 302 and extending through an outlet port 502 in the distal end 310 of the lead 302, into an inlet port 504 in the bend 326 of the lead 314, and into the distal end 322 of the lead 314. When the insertion rod 406 is inserted through the distal ends 310 and 322 of leads 302 and 314, respectively, the stylet 402 can be used to jointly guide both leads 302 and 314 during implantation. In at least some embodiments, one or more of the ports 502 and 504 are configured and arranged to remain sealed when the insertion rod 406 is not extending through the ports 502 and 504. For example, the ports can be made using a self-sealing material, such as silicone, polyurethane, hydrogel, rubber, polymers, latex, reinforced plastics, polymeric resins, and the like, which closes the ports when the insertion rod 406 is removed. In at least some embodiments, the lead 314 further includes an outlet port (not shown) on the distal end 322 through which the insertion rod 406 may be extended to allow additional leads to be jointly implanted along with the leads 302 and 314 by the insertion rod 406. In at least some embodiments, the outlet ports may be permanently or removably sealed. In at least some embodiments, when an insertion rod 406 is extended through multiple leads, the distal-most lead may not include an outlet port.

Figures 6A, 6B:
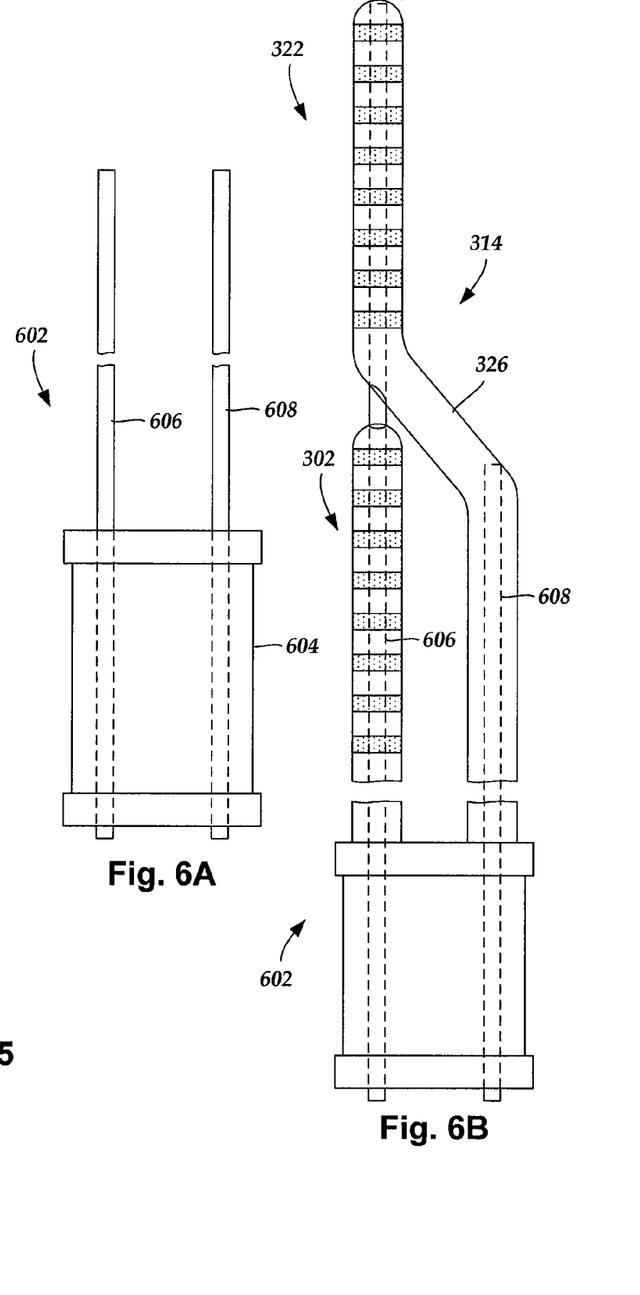
FIG. 6A is a schematic side view of another embodiment of a stylet of an electrical-stimulation implantation system, according to the invention.
FIG. 6B is a schematic side view of the embodiment of the stylet of the electrical-stimulation implantation system shown in FIG. 6A with two insertion rods, each insertion rod inserted in a proximal end of a lead, according to the invention.

In at least some embodiments, a stylet may include multiple insertion rods that can be disposed in multiple leads during implantation. FIG. 6A shows a schematic side view of another embodiment of a stylet 602. The stylet 602 includes a handle 604, an insertion rod 606, and an insertion rod 608. The number of insertion rods on the stylet 602 may vary. For example, there can be one, two, three, four, or more insertion rods. As will be recognized, other numbers of insertion rods may also be used. In at least some embodiments, the stylet includes one or more insertion rods with distal portions that split into two or more separate insertion rods.

FIG. 6B shows a schematic side view of the insertion rod 606 inserted into a lumen (not shown) disposed in the lead 302 and the insertion rod 608 inserted into a lumen (not shown) disposed in the lead 314. In some embodiments, the insertion rod 606 is only inserted into the lead 302. In other embodiments, as shown in FIG. 6B, the insertion rod 606 extends into the distal end 322 of the lead 314 in a manner similar to the insertion rod 406 shown in FIG. 5. In some embodiments, as shown in FIG. 6B, the insertion rod 608 is inserted into the lead 314 up to a proximal portion of the bend 326. In other embodiments, the insertion rod 608 is inserted in the lead 314 to the distal end 322 of the lead 314, thus straightening the bend 326 while the insertion rod 608 is inserted within the bend 326.

Figure 7A:
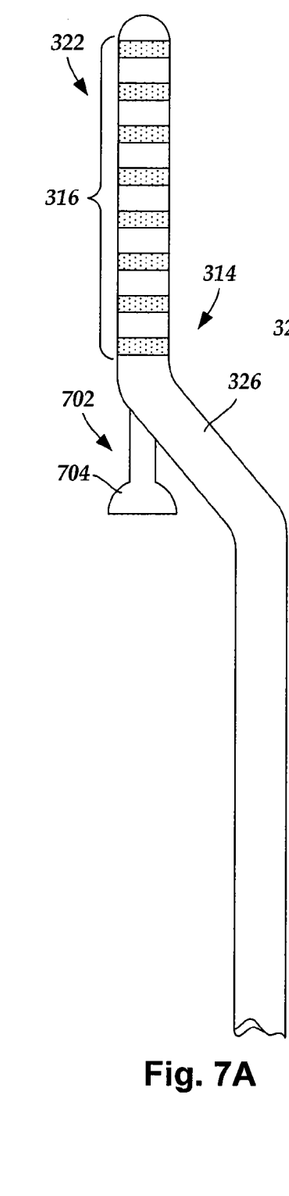
FIG. 7A is a schematic side view of one embodiment of a distal end of a lead with a plurality of electrodes and a bend disposed in the lead proximal to the plurality of electrodes, the lead also including a coupling mechanism with a guide channel coupled to the bend, according to the invention.

In at least some embodiments, a coupling mechanism may be used to removably couple two or more leads together in relative positions that linearly align the electrodes disposed on the leads to form a combination electrode array along a combination electrode axis. FIG. 7A shows a schematic side view of one embodiment of a coupling mechanism 702 coupled to the lead 314. The coupling mechanism 702 includes a guide channel 704 oriented so that when a distal end of another lead is coupled to the guide channel 704, a plurality of electrodes disposed on the distal end of the other lead align with the plurality of electrodes 316 disposed on the distal end 322 of the lead 314.

Figure 7B:
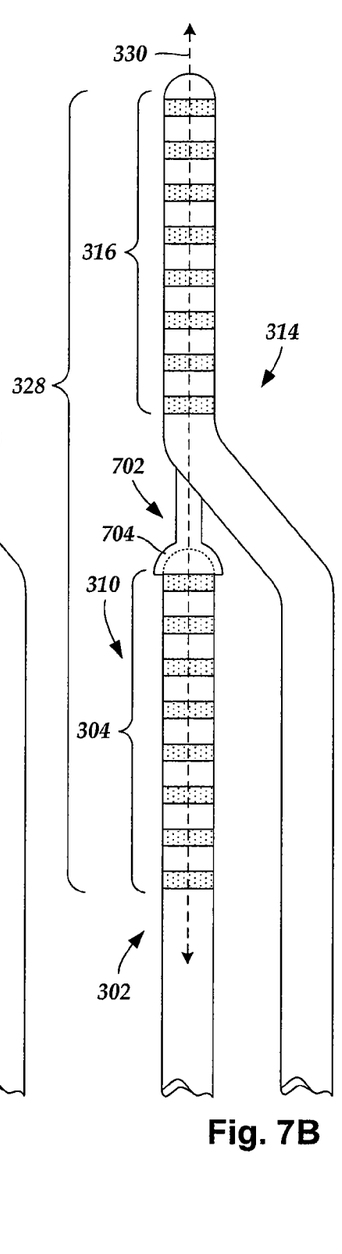
FIG. 7B is a schematic side view of one embodiment of a distal end of a lead with a plurality of electrodes, a portion of the lead distal to the plurality of electrodes coupled to the coupling mechanism of the lead shown in FIG. 7A so that the plurality of electrodes of each of the leads linearly align to form a combination electrode array, according to the invention.

FIG. 7B shows a schematic side view of one embodiment of the distal end 310 of the lead 302 attached to the guide channel 704 of the coupling mechanism 702 coupled to the lead 314. The plurality of electrodes 304 disposed on the lead 302 are linearly aligned with the plurality of electrodes 316 disposed on the lead 314 along the combination electrode axis 330 to form the combination electrode array 328. In a preferred embodiment, the distal end 310 of the lead 302 is coupled to the guide channel 702 so that the plurality of electrodes 304 of the lead 302 are not obstructed by the guide channel 704.

Figure 7C:
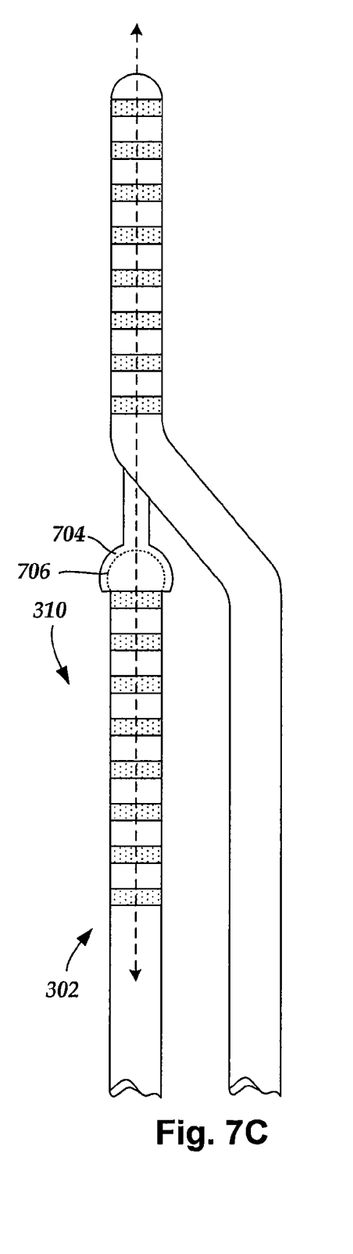
FIG. 7C is a schematic side view of another embodiment of a distal end of a lead with a plurality of electrodes, a portion of the lead distal to the plurality of electrodes coupled to a coupling mechanism of the lead shown in FIG. 7A so that the plurality of electrodes of each of the leads linearly align to form a combination electrode array, according to the invention.

In some embodiments, the distal end 310 of the lead 302 couples to the guide channel 704 by forming an interference fit with the guide channel 704. In some embodiments, the distal end 310 of the lead 302 includes protrusions, such as barbs or rings which mate with inset regions, such as ribs inside the guide channel 704. In some embodiments, the distal end 310 of the lead 302 includes a ball that mates with a socket in the guide channel 704, or vice versa. FIG. 7C shows a schematic side view of an embodiment of the distal end 310 of the lead 302 attached to the guide channel 704. As shown in FIG. 7C, the distal end 310 of the lead 302 includes a ball 706 mated with a socket-shaped guide channel 704. Many other corresponding distal end/guide channel shapes may be used. For example, the distal end 310 of the lead 302 can have a tubular shape that mates with a cylindrical-shaped guide channel 704, or vice versa.

Figures 8A, 8B, 9A, 9B:
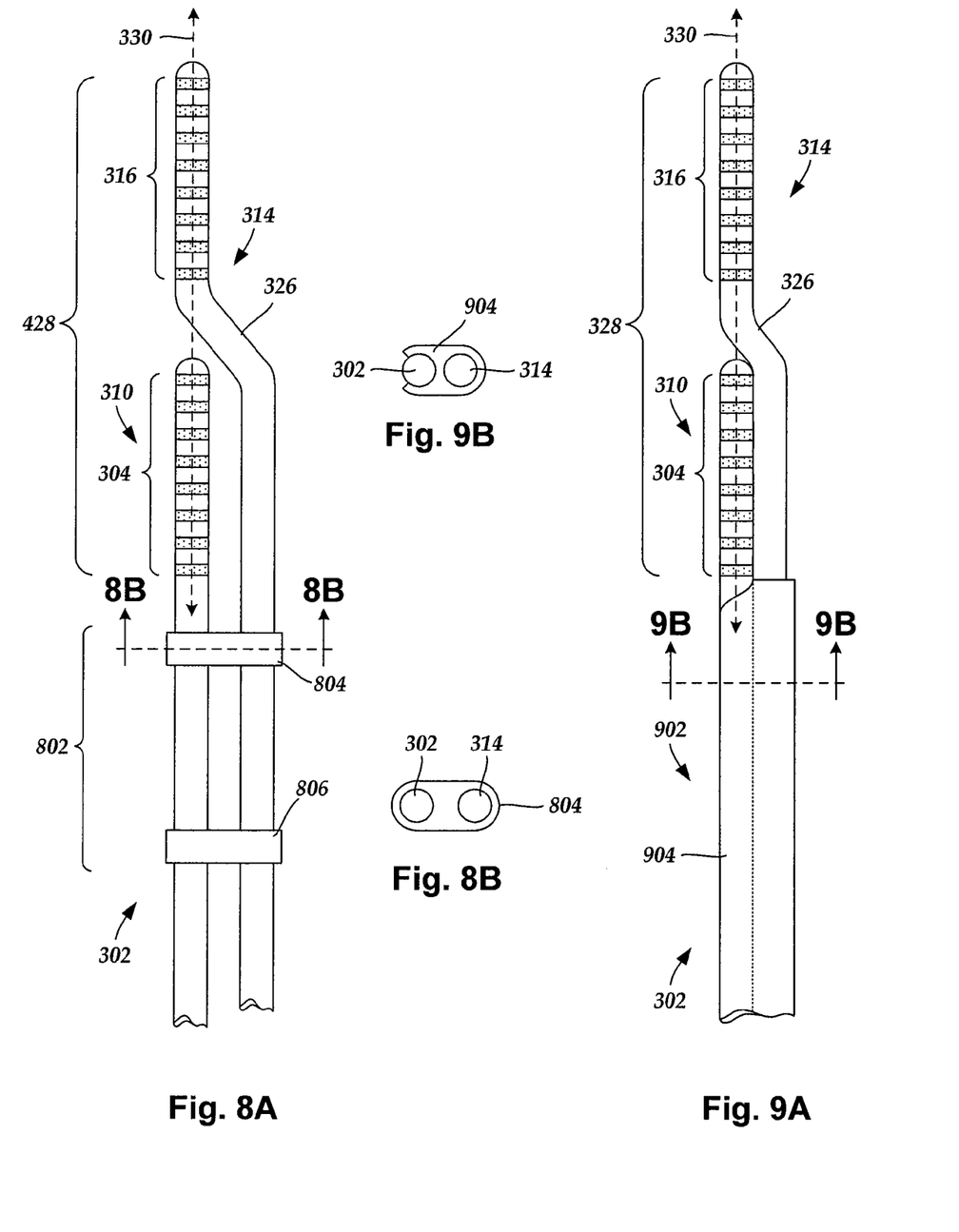
FIG. 8A is a schematic side view of one embodiment of a distal end of a first lead with a first plurality of electrodes disposed in a first electrode axis coupled to a distal end of a second lead second plurality of electrodes disposed in a second electrode axis by a coupling mechanism so that the first electrode axis aligns linearly with the second electrode axis, according to the invention.
FIG. 8B is a schematic transverse cross-sectional view of the two leads shown in FIG. 8A coupled together by a coupling mechanism, according to the invention.
FIG. 9A is a schematic side view of another embodiment of a distal end of a first lead with a first plurality of electrodes disposed in a first electrode axis coupled to a distal end of a second lead second plurality of electrodes disposed in a second electrode axis by a coupling mechanism so that the first electrode axis aligns linearly with the second electrode axis, according to the invention.
FIG. 9B is a schematic transverse cross-sectional view of the two leads shown in FIG. 9A coupled together by a coupling mechanism, according to the invention.

In at least some embodiments, a coupling mechanism includes one or more cuffs mounted to an outer surface of a central region of one or more leads. The cross-sectional shape of the one or more cuffs preferably matches the cross-sectional shape of the leads. One or more leads may be removably coupled to one another by sliding a distal end of one or more leads through one or more cuffs coupled on one or more other leads. FIG. 8A shows a schematic side view a coupling mechanism 802 that includes cuffs 804 and 806 coupled to the lead 314 through which the distal end 310 of the lead 302 has been slid until the distal end 310 of the lead 302 is in proximity to the bend 326 of the lead 314 and the cuffs 804 and 806 are contacting the lead 302. In a preferred embodiment, the coupling mechanism 802 guides or holds the lead 302 in position so that the plurality of electrodes 304 disposed on the lead 302 are linearly aligned with the plurality of electrodes 316 disposed on the lead 314 along the combination electrode axis 330 to form the combination electrode array 328.

Any number of cuffs 804 and 806 in the coupling mechanism 802 can be selected. For example, there can be one, two, three, four, five, six, eight, ten, or more loops in a coupling mechanism 802. As will be recognized, other numbers of cuffs may also be used. The cuffs may have different cross-sectional shapes. In at least some embodiments, the cross-sectional shapes of each of the cuffs are selected to correspond with the cross-sectional shapes of leads. The cuffs may be many different widths. For example, in some embodiments a single cuff is a width that is equal to the entire length of the portion of the lead 314 proximal to the electrodes and distal to the terminals, while in other embodiments the width of a cuff is narrower than the diameter of the cuff. In a preferred embodiment, the plurality of electrodes 304 on the lead 302 are unobstructed by the coupling mechanism 802. FIG. 8B shows a schematic transverse cross-sectional view of one embodiment of the leads 302 and 315 disposed in the cuff 804.

In at least some embodiments, a coupling mechanism includes one or more grooves coupled to one or more leads. One or more leads may be removably coupled to one another by sliding a distal end of one or more leads through one or more grooves coupled on one or more other leads. FIG. 9A shows a schematic side view a coupling mechanism 902 that includes a groove 904 coupled to the lead 314 through which the distal end 310 of the lead 302 has been slid until the distal end 310 of the lead 302 is in proximity to the bend 326 of the lead 314. In a preferred embodiment, the plurality of electrodes 304 are unobstructed by the groove 904 and are guided into position by the groove 904 so that the plurality of electrodes 304 disposed on the lead 302 are linearly aligned with the plurality of electrodes 316 disposed on the lead 314 along the combination electrode axis 330 to form the combination electrode array 328.

In at least some embodiments, a lead with electrodes may include two grooves extending along at least a portion of the longitudinal length of the lead on opposite sides so that the electrodes of at least two other leads may align linearly with the electrodes disposed on the lead with the two grooves. The grooves may also be many different lengths. For example, as shown in FIG. 9A, in some embodiments a single groove is equal in length to the entire length of the lead proximal to the electrodes and distal to the terminals, while in other embodiments the length of a groove is less than the diameter of the groove. In at least some embodiments, a groove may include one or more open portions along the length of the groove. In the embodiment shown in FIG. 9A, the groove 904 is coupled to the lead 314 and the lead 302 may be slid along the length of the groove 904. In alternate embodiments, the groove 904 is coupled to the lead 302 and the lead 314 may be slid along the length of the groove 904. FIG. 9B shows a schematic transverse cross-sectional view of one embodiment of the leads 302 and 314 disposed in the groove 904.

Figure 10A:
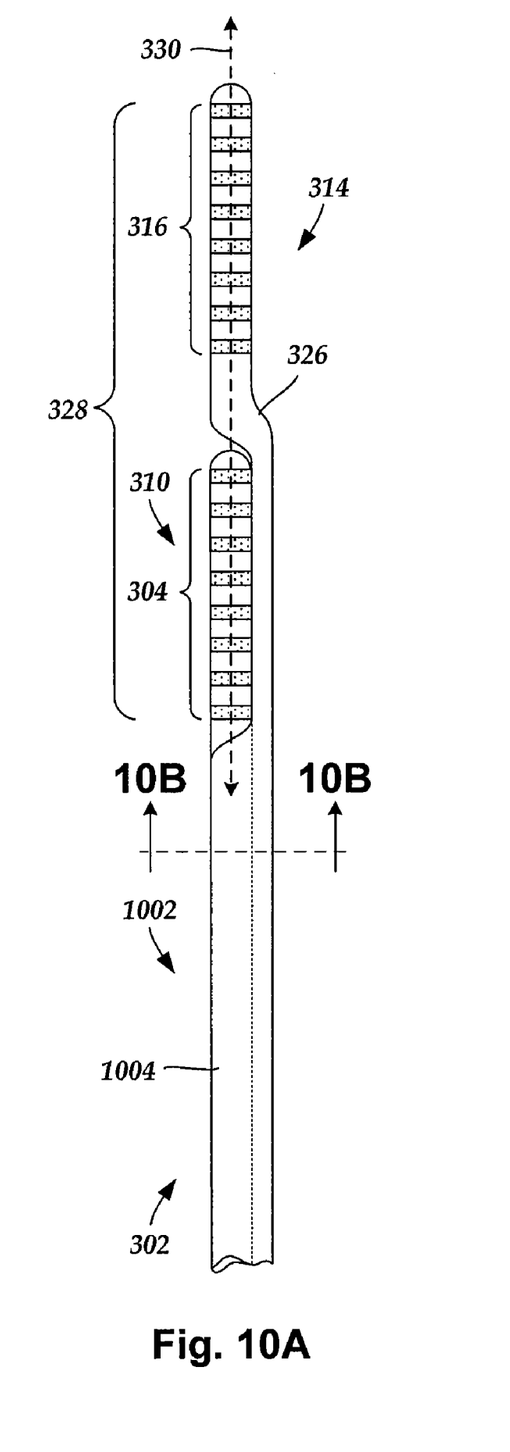
FIG. 10A is a schematic side view of a third embodiment of a distal end of a first lead with a first plurality of electrodes disposed in a first electrode axis coupled to a distal end of a second lead second plurality of electrodes disposed in a second electrode axis by a coupling mechanism so that the first electrode axis aligns linearly with the second electrode axis, according to the invention.
Figure 10B:
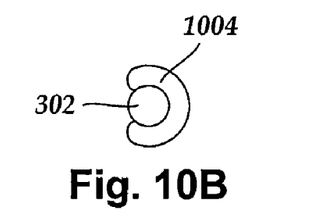
FIG. 10B is a schematic transverse cross-sectional view of the two leads shown in FIG. 10A coupled together by a coupling mechanism, according to the invention.

In at least some embodiments, at least a portion of a lead has a C-shaped cross-sectional shape that can be used as a groove through which a distal end of another lead may be slid along. FIG. 10A shows a schematic side view a coupling mechanism 1002 that includes a groove 1004 coupled to the lead 314 through which the distal end 310 of the lead 302 has been slid until the distal end 310 of the lead 302 is in proximity to the bend 326 of the lead 314. In a preferred embodiment, the plurality of electrodes 304 are unobstructed by the groove 1004 and are guided into position by the groove 1004 so that the plurality of electrodes 304 disposed on the lead 302 are linearly aligned with the plurality of electrodes 316 disposed on the lead 314 along the combination electrode axis 330 to form the combination electrode array 328. FIG. 10B shows a schematic transverse cross-sectional view of one embodiment of the lead 302 disposed in the groove 1004. One advantage of providing a lead with a C-shaped portion, such as the C-shaped portion of the lead 314 shown in FIGS. 10A and 10B, is that the combined diameter of the coupled leads 302 and 314 shown in FIGS. 10A and 10B are less than the combined diameter of the coupled leads 302 and 314 shown in FIGS. 8A-9B.

In at least some embodiments, a coupling mechanism may include various combinations of cuffs, guide channels, and grooves. In at least some embodiments, when one or more coupling mechanisms are utilized to removably couple two or more leads, the leads may be either implanted separately or jointly implanted. In some embodiments, a lead with a coupled coupling mechanism is implanted. Subsequently, one or more other leads may be coupled to the already-implanted coupling mechanism during one or more subsequent implantations. For example, a lead with a guide channel may be implanted. Subsequently, a second lead may be implanted so that the distal end of the channel-less lead is attached to the guide channel. In other embodiments, one or more leads without coupling mechanisms may be coupled to one or more leads with mechanisms prior to implantation into a patient. For example, a lead without one or more cuffs can be inserted into the one or more cuffs of a lead with cuffs. The coupled leads may subsequently be implanted into a patient.

Figure 11:
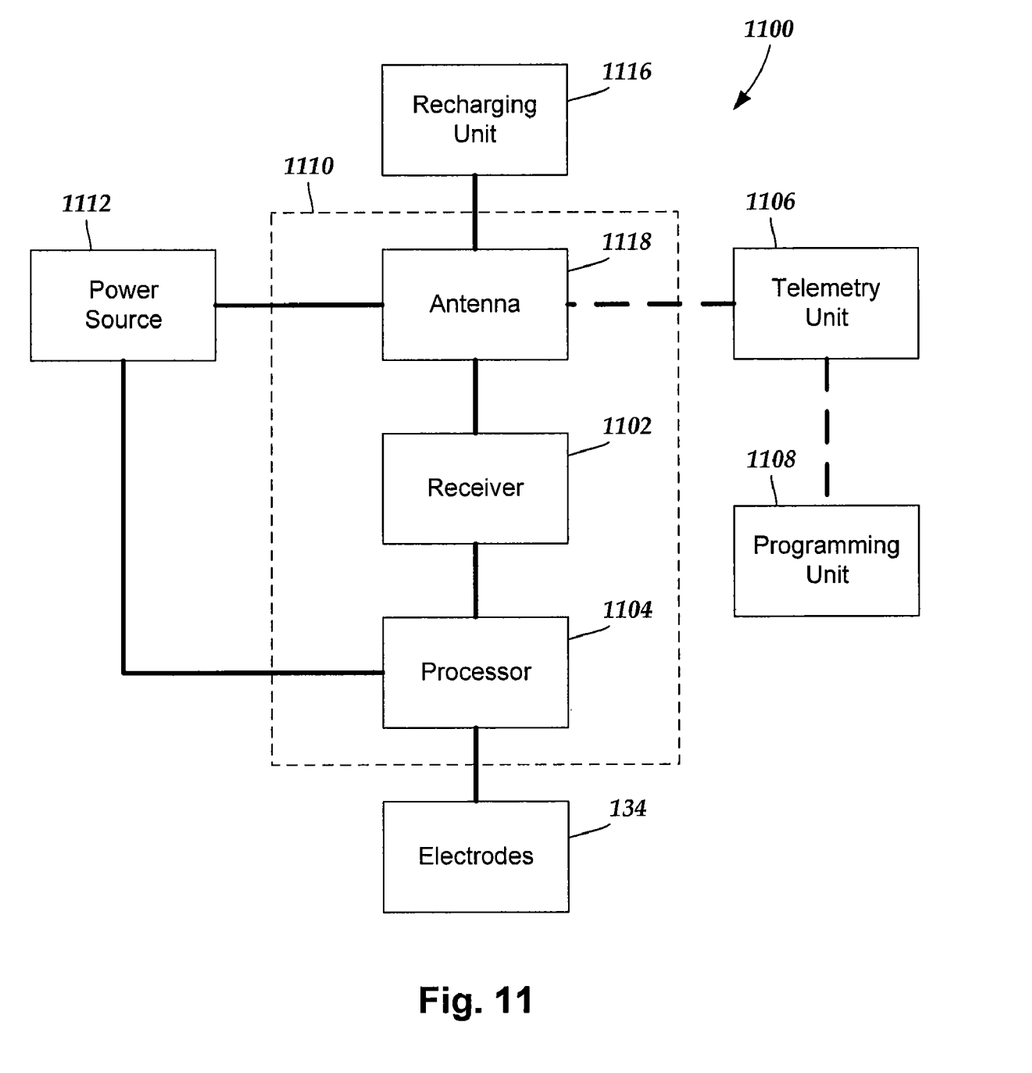
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A multi-lead system comprising:
    a first lead comprising
        a first lead body having a distal end, a proximal end, a longitudinal length, and an outer surface,
        a first plurality of electrodes disposed along the distal end of the first lead with the first plurality of electrodes arranged along a first electrode axis,
        a first plurality of terminals disposed along the proximal end of the first lead,
        a first stylet lumen extending along the longitudinal length of the first lead body from the proximal end to the distal end of the first lead body,
        a first outlet port defined distally from the first plurality of electrodes, the first outlet port providing an opening between the first stylet lumen and the outer surface of the first lead body, and
        a first plurality of conductor wires extending along the first lead and coupling the first plurality of electrodes electrically to the first plurality of terminals;
    a second lead comprising
        a second lead body having a distal end, a proximal end, and at least one bend formed between the distal end and the proximal end of the second lead body,
        a second plurality of electrodes disposed along the distal end of the second lead with the second plurality of electrodes arranged along a second electrode axis,
        a second plurality of terminals disposed along the proximal end of the second lead, and
        a second stylet lumen extending distally along the second lead body from a second inlet port defined in the at least one bend,
        a second plurality of conductor wires extending along the second lead and coupling the second plurality of electrodes electrically to the second plurality of terminals; and
    a stylet configured and arranged for concurrent insertion into both the first stylet lumen and the second stylet lumen with the stylet extending between the first stylet lumen and the second stylet lumen via the first outlet port and the second inlet port, wherein when the stylet is inserted into both the first stylet lumen and the second stylet lumen the first electrode axis is aligned linearly with the second electrode axis to form a combination electrode axis, the combination electrode axis comprising each electrode of the first plurality of electrodes and each electrode of the second plurality of electrodes aligned along a common axis.

2. The multi-lead system of claim 1, wherein the first lead body also comprises at least one bend.

3. The multi-lead system of claim 2, wherein the at least one of bend of the first lead body is configured and arranged to at least partially straighten when the stylet is inserted into the first stylet lumen.

4. The multi-lead system of claim 1, wherein the stylet comprises a handle and a first insertion rod coupled to the handle, the first insertion rod configured and arranged for concurrent insertion into both the first stylet lumen and the second stylet lumen via the first outlet port and the second stylet lumen.

5. The multi-lead system of claim 4, wherein the second stylet lumen additionally extends from the second inlet port to the proximal end of the second lead body.

6. The multi-lead system of claim 5, wherein the stylet further comprises a second insertion rod coupled to the handle, the second insertion rod configured and arranged for insertion into the second stylet lumen from the proximal end of the second lead body to the at least one bend.

7. The multi-lead system of claim 6, wherein the second stylet lumen is configured and arranged to concurrently receive both the first insertion rod and the second insertion rod.

8. An electrical stimulating system comprising:
    the multi-lead system of claim 1;
    at least one control module configured and arranged to electrically couple to each of the leads of the multi-lead system, the at least one control module comprising
        a housing, and
        an electronic subassembly disposed in the housing; and
    a connector for receiving at least one of the leads of the multi-lead system, the connector comprising
        a connector housing defining at least one port for receiving the proximal end of at least one of the lead bodies of the multi-lead system, and
        a plurality of connector contacts disposed in the connector housing, the connector contacts configured and arranged to couple to at least one of the plurality of terminals disposed along the proximal end of at least one of the lead bodies of the multi-lead system when the proximal end of at least one of the lead bodies of the multi-lead system is disposed in the connector housing.

9. The electrical stimulating system of claim 8, further comprising a coupling mechanism coupling the first lead body to the second lead body with the first plurality of electrodes of the first lead body disposed in proximity to the at least one bend of the second lead body.

10. A method for stimulating patient tissue, the method comprising:
    providing the multi-lead system of claim 1;
    implanting the first lead of the multi-lead system into a patient;
    implanting the second lead of the multi-lead system into the patient;
    coupling the first and second leads to at least one control module; and
    providing electrical signals from the at least one of the control module to electrically stimulate patient tissue using at least one electrode of at least one of the first plurality of electrodes or the second plurality of electrodes.

11. The method of claim 10, wherein implanting the first lead and the at least one second lead into the patient comprises inserting the stylet into both the first stylet lumen and the second stylet lumen with the stylet extending between the first outlet port and the second inlet port.

12. The method of claim 11, wherein inserting the stylet into both the first stylet lumen and the second stylet lumen with the stylet extending between the first outlet port and the second inlet port comprises inserting a first insertion rod of the stylet into both the first stylet lumen and the second stylet lumen with the stylet extending between the first outlet port and the second inlet port.

13. The method of claim 12, further comprising inserting a second insertion rod of the stylet into a portion of the second stylet lumen proximal to the at least one bend of the second lead body.

14. A multi-lead system comprising:
a first lead comprising
  a first lead body having a distal end and a proximal end,
  a first plurality of electrodes disposed along the distal end of the first lead with the first plurality of electrodes arranged along a first electrode axis,
  a first plurality of terminals disposed along the proximal end of the first lead, and
  a first plurality of conductor wires extending along the first lead and coupling the first plurality of electrodes electrically to the first plurality of terminals;
a second lead comprising
  a second lead body having a distal end, a proximal end, and at least one bend formed between the distal end and the proximal end of the second lead body,
  a second plurality of electrodes disposed along the distal end of the second lead with the second plurality of electrodes arranged along a second electrode axis,
  a second plurality of terminals disposed along the proximal end of the second lead, and
  a second plurality of conductor wires extending along the second lead and coupling the second plurality of electrodes electrically to the second plurality of terminals; and
a coupling mechanism coupling the first lead body to the second lead body with the first plurality of electrodes of the first lead body disposed in proximity to the at least one bend of the second lead body, the coupling mechanism comprising at least one guide channel extending from the at least one bend of the second lead, the at least one guide channel configured and arranged to mate with the distal end of the first lead body by coupling the distal end of the first lead body to the at least one guide channel with the second electrode axis aligned linearly with the first electrode axis to form a combination electrode axis, the combination electrode axis comprising each electrode of the first plurality of electrodes and each electrode of the second plurality of electrodes aligned along a common axis.

15. The multi-lead system of claim 14, wherein the distal end of the first lead body removably attaches to the at least one guide channel by an interference fit between the distal end of the first lead body and the at least one guide channel.

16. The multi-lead system of claim 14, wherein either the distal end of the first lead body or the at least one guide channel further comprises a ball and the other of the distal end of the first lead body or the at least one guide channel further comprises a socket configured and arranged to removably couple with the ball.

17. The multi-lead system of claim 14, wherein either the distal end of the first lead body or the at least one guide channel further comprises at least one protrusion and the other of the distal end of the first lead body or the at least one guide channel further comprises at least one inset region configured and arranged to removably couple with the at least one protrusion.

18. A multi-lead system comprising:
a first lead comprising
  a first lead body having a distal end and a proximal end,
  a first plurality of electrodes disposed along the distal end of the first lead body with the first plurality of electrodes arranged along a first electrode axis,
  a first plurality of terminals disposed along the proximal end of the first lead body, and
  a first plurality of conductor wires extending along the first lead body and coupling the first plurality of electrodes electrically to the first plurality of terminals;
a second lead comprising
  a second lead body having a distal end, a proximal end, and at least one bend formed between the distal end and the proximal end of the second lead body,
  a second plurality of electrodes disposed along the distal end of the second lead body with the second plurality of electrodes arranged along a second electrode axis,
  a second plurality of terminals disposed along the proximal end of the second lead body, and
  a second plurality of conductor wires extending along the second lead body and coupling the second plurality of electrodes electrically to the second plurality of terminals; and
a coupling mechanism coupling the first lead body to the second lead body with the first plurality of electrodes of the first lead body disposed in proximity to the at least one bend of the second lead body, the coupling mechanism coupled to the first lead body proximal to the first plurality of electrodes, and the coupling mechanism coupled to the second lead body proximal to the at least one bend;
wherein the at least one bend aligns the second electrode axis with the first electrode axis to form a combination electrode axis, the combination electrode axis comprising each electrode of the first plurality of electrodes and each electrode of the second plurality of electrodes aligned along a common axis.

19. The multi-lead system of claim 18, wherein the coupling mechanism comprises at least one attachment cuff mounted to the first lead or the second lead, the at least one attachment cuff configured and arranged to mate with the other of the first lead or the second lead by passing through the at least one attachment cuff.

20. The multi-lead system of claim 18, wherein the coupling mechanism comprises at least one groove extending along at least a portion of the first lead or the second lead, the at least one groove configured and arranged to mate with the other of the first lead or the second lead by passing through the at least one groove.

* * * * *